United States Patent [19]

Williams et al.

[11] 4,223,808
[45] Sep. 23, 1980

[54] REFILLABLE DISPENSING DEVICE HAVING WIPER SEAL

[75] Inventors: John E. Williams, Del Mar; Lester H. Rabe, Palm Deserts, both of Calif.

[73] Assignee: Spray Safe Company, Inc., Fullerton, Calif.

[21] Appl. No.: 926,639

[22] Filed: Jul. 21, 1978

[51] Int. Cl.² ............................................. B65D 17/24
[52] U.S. Cl. ...................................... 222/88; 222/387; 222/327
[58] Field of Search ............... 222/327, 326, 341, 340, 222/387, 88, 1; 220/93; 221/198; 53/470

[56] References Cited

U.S. PATENT DOCUMENTS

| | | | |
|---|---|---|---|
| 2,506,833 | 5/1950 | Hunter | 222/340 |
| 2,625,302 | 1/1953 | Mahoney | 222/341 UX |
| 2,758,758 | 8/1956 | Schimpf | 222/327 |
| 3,250,442 | 5/1966 | Bell et al. | 222/327 |
| 3,847,304 | 11/1974 | Cohen | 222/326 X |

*Primary Examiner*—David A. Scherbel

*Attorney, Agent, or Firm*—Burns, Doane, Swecker & Mathis

[57] ABSTRACT

A readily refillable dispensing device for dispensing liquids and other fluids without a use of gaseous propellants includes an outer casing having an aerosol valve assembly, a refill assembly which is received within the outer case and an end cap. The refill assembly includes a rigid cylindrical sleeve, a piston slidably received within the cylindrical sleeve, a rubber wiper seal, and a coil spring for biasing the piston towards an upper portion of the refill assembly. The piston includes at least one depending lock hook which releasably engages a lower sleeve closure of the cylindrical sleeve. The piston is released from the lower sleeve closure by threading the bottom cap onto the outer case. A cam of the bottom cap urges the at least one depending lock hook out of engagement with the lower sleeve closure. The wiper seal is preferably made of a resilient material such as rubber or neoprene and effectively seals an interior chamber of the refill assembly.

16 Claims, 8 Drawing Figures

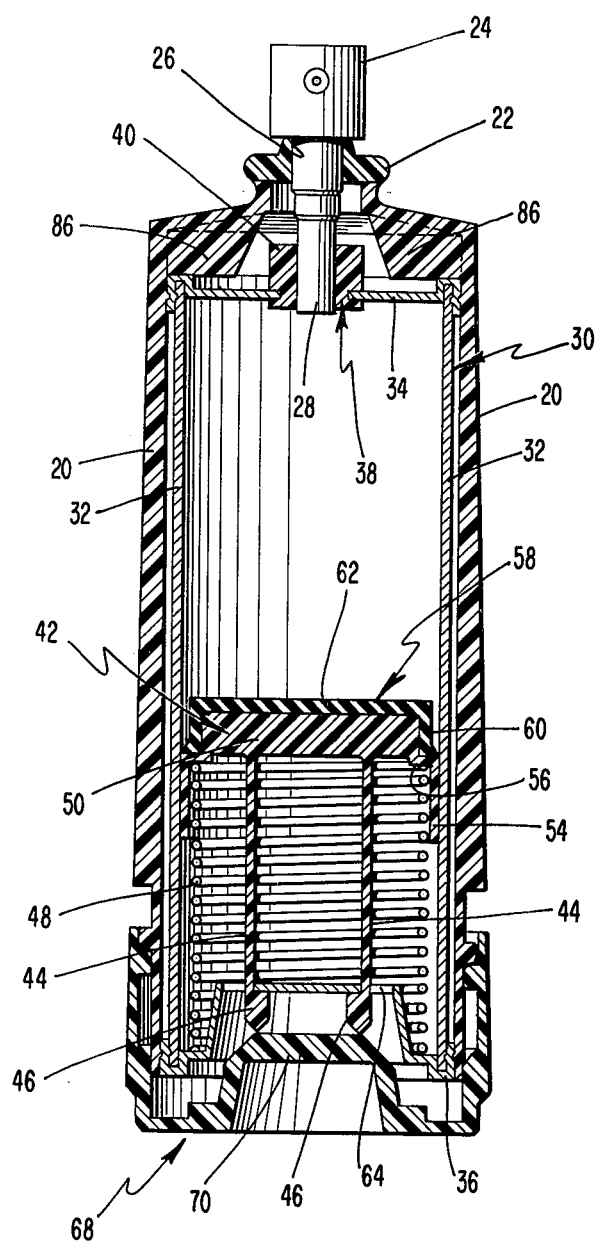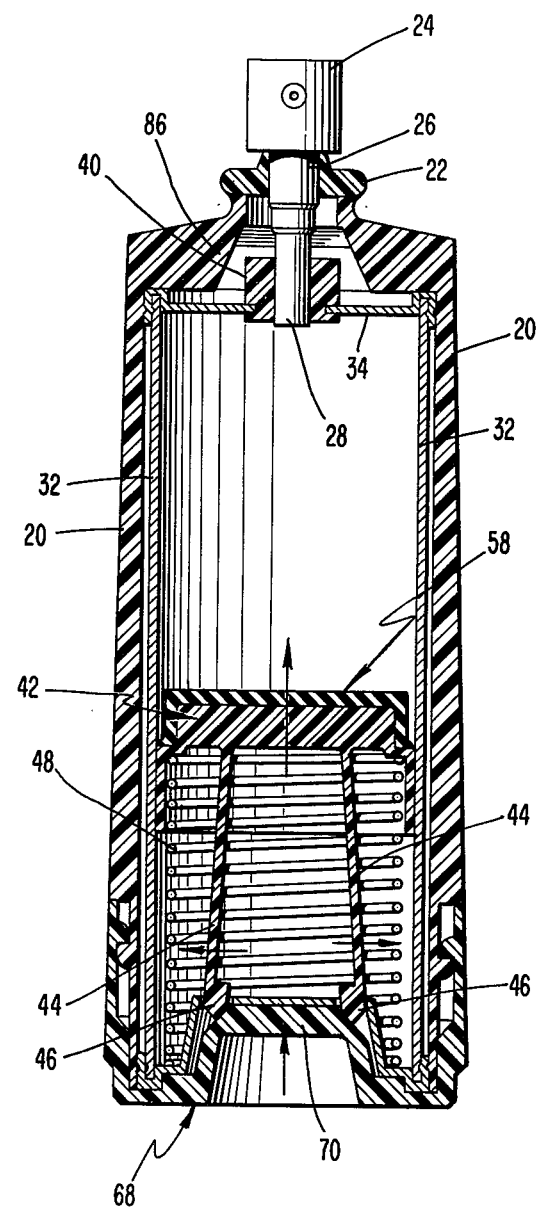
Fig. 1
Fig. 2

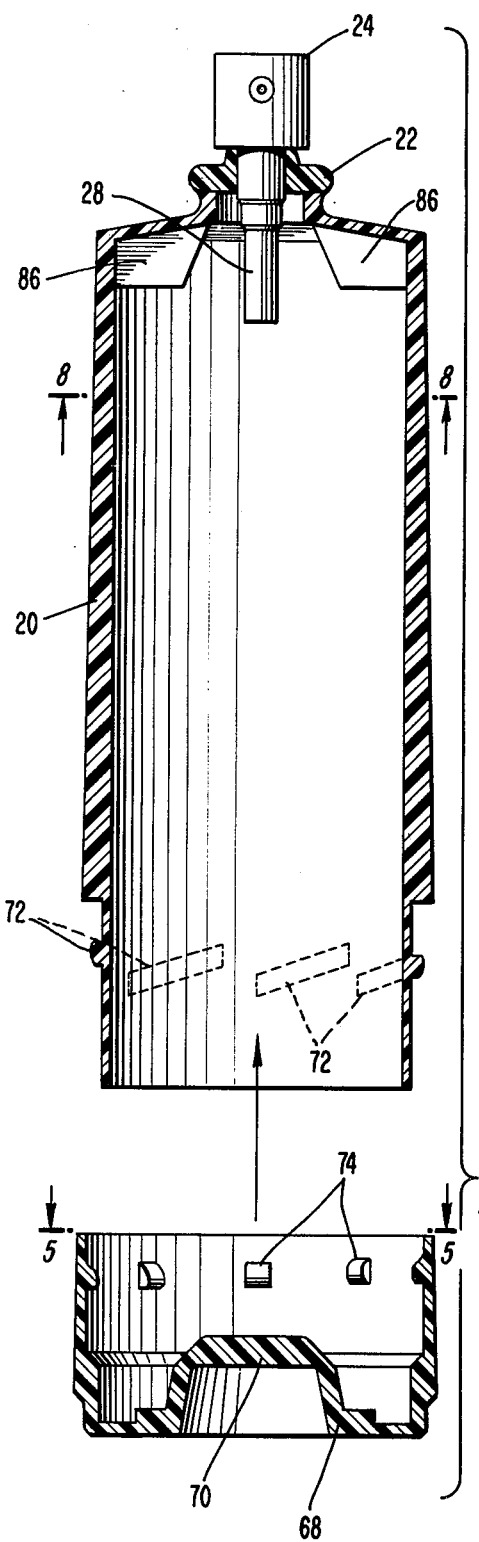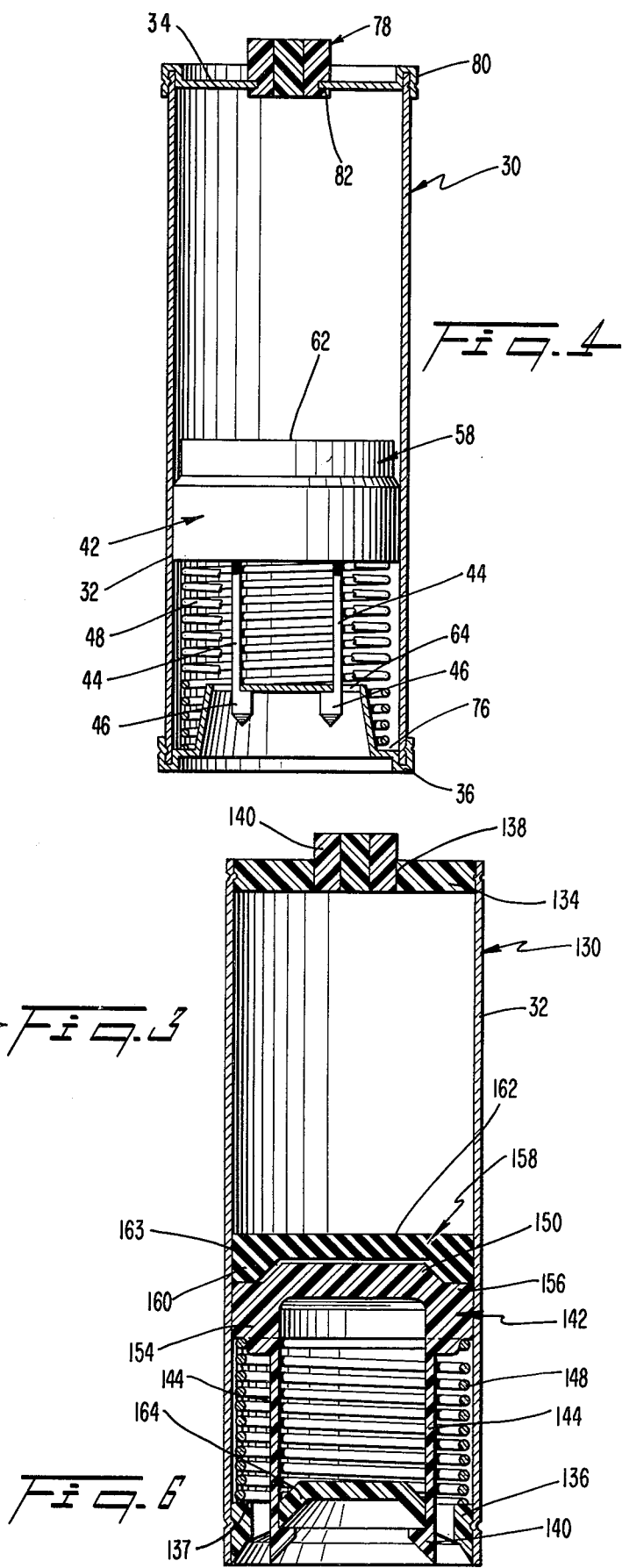

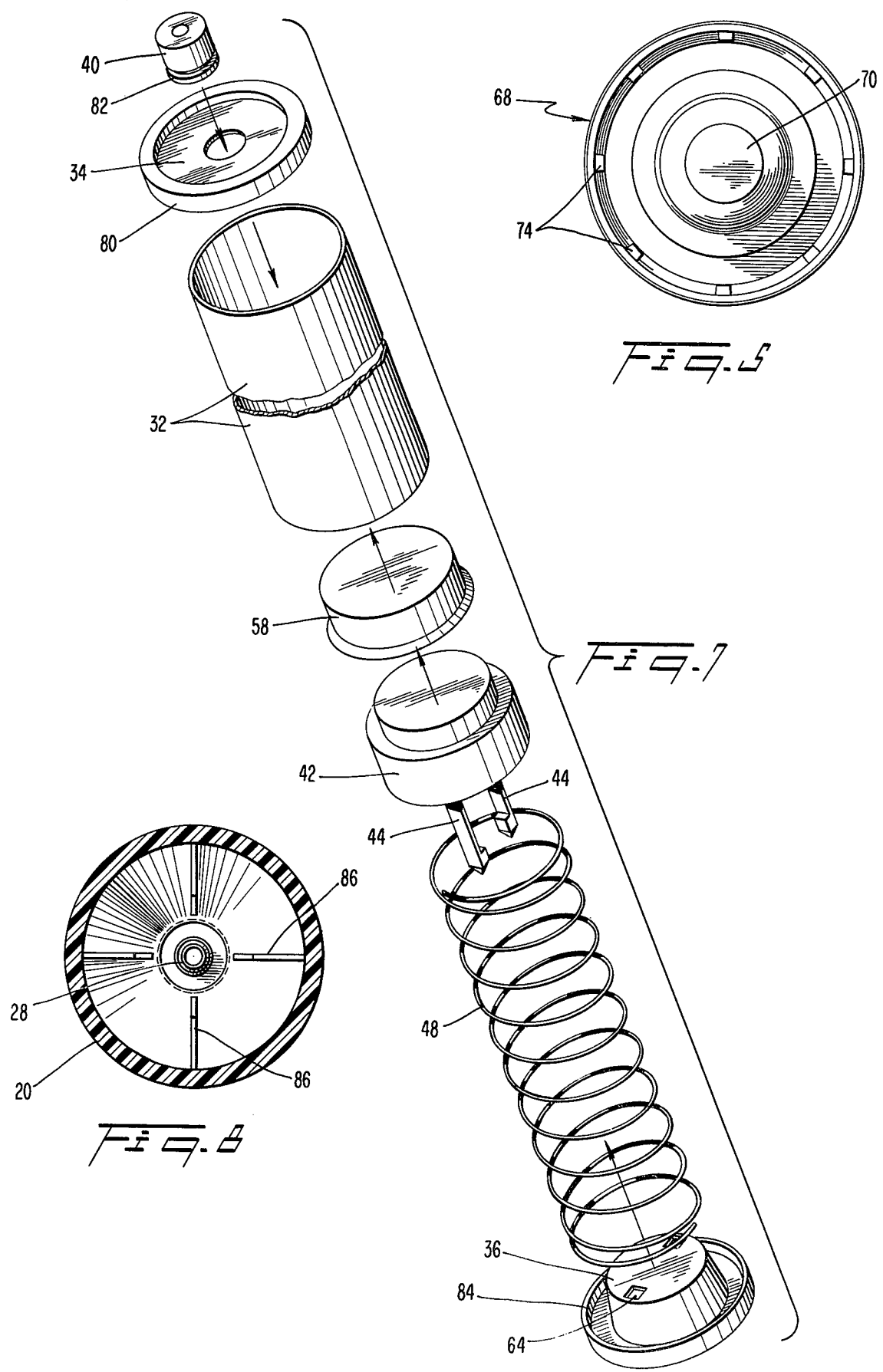

REFILLABLE DISPENSING DEVICE HAVING WIPER SEAL

BACKGROUND AND SUMMARY OF THE PRESENT INVENTION

The present invention relates to a device for the dispensing of fluid materials such as liquids, creams, gels and pastes under higher than atmospheric pressure. More particularly, the present invention relates to a device which is readily refillable by inserting a refill assembly into an outer casing for dispensing such cosmetics as perfumes, hairsprays, creams and lotions and also such materials as household cleaners and food materials.

In the development of the art, the pressure for dispensing such materials customarily has been supplied by incorporating in the container, along with the fluid material to be dispensed, a pressurized propellant such as a fluorocarbon aerosol whose vapor pressure was such as to force the liquid material from the container when a dispensing valve was opened. While these arrangements were and are operable, there are substantial objections to their use. In the first place, their use presents a serious environmental hazard since there is substantial evidence that the aerosol propellants are destructive of the ozone belt which protects the earth from harmful ultra violet rays. A second objection is that such aerosol dispenser is used only once and then discarded with the resultant waste of a container casing and valve which represents not only a waste of materials and energy but also a waste of money. The disposal of the discarded aerosol dispenser constitutes a major, expensive chore for society.

It is accordingly apparent that the above disadvantages could be avoided if the fluid material were placed in a refill assembly which would be readily inserted in a housing or outer case so that the fluid material might be dispensed by the application of an outside pressure which might be applied by a spring.

An object of the present invention is to provide an improved device for dispensing fluid material in the form of a spray, mist or stream under suitable pressure, said device being simple, inexpensive, rugged, economical of materials and readily refillable by the user.

The device of the invention comprises an outer cylindrical casing topped by a cover having therein an aerosol valve assembly; a disposable refill assembly including a rigid cylindrical sleeve and dimensioned to be readily insertable in and removable from said casing into and out of communication with said aerosol valve; a biased piston assembly adapted to be received in a lower portion of the rigid cylindrical sleeve and to bear against a lower end of a wiper seal, the wiper seal effectively sealing a fluid chamber of the refill assembly, and a bottom cover/cam adapted to be releasably secured to a lower end of the outer casing and, when so secured, so as to release the biased piston to urge the wiper seal upwardly to pressurize the fluid chamber. A locking means, for securing the piston to a lower sleeve closure of the cylindrical sleeve is provided by a bayonet lock arrangement including at least one locking detent slot in the lower closure of the cylindrical casing cooperating with at least one locking pin extending axially from the piston.

The entire biased piston refill assembly is secured in the outer casing by the bottom cover. The bottom cover is threaded onto the outer casing to secure the refill assembly in the outer casing while simultaneously releasing the piston from the lower sleeve closure.

The fluid is provided inside the rigid sleeve (or "liner" of the refill assembly) so as to facilitate insertion of the refill assembly into the container. The sleeve extends to the lower opening of the outer casing, when the bottom cap is off, so that the refill assembly can be reached for easy removal when the fluid product chamber is empty. The upper end of the sleeve is sealed by an upper sleeve closure and the product chamber is effectively sealed by the wiper seal to permit pressurization of the product chamber by the biased piston. The center of the upper sleeve closure contains an opening incorporating an annular deformable sealing member through which, when the stem of a metering valve is inserted, the product chamber communicates with the valve by sliding the same through the sealing member. In this way the contents of the product chamber are readily dispensed.

When the biased piston is released by rotational movement of the bottom cover/cam, the entire product chamber is pressurized. In this way, refilling the device is simplified.

To assemble the device, only a single refill assembly including product chamber, wiper seal, biased piston spring and releasable locking means is inserted in the outer case. The biased piston is readily released by securely threading the bottom cap onto the outer case. In this way, refilling the device is an easy procedure which does not involve physical contact or exposure with the fluid product.

At least one lock hook extends downwardly from the bottom of the biased plunger. The hook cooperates with at least one detent slot in the lower sleeve closure of the cylindrical sleeve.

The cam-cover is the last part to be assembled when refilling the dispensing device. It comprises a cap containing in the center a raised portion. When the cam-cover is substantially fully threaded on the outer case, the raised portion acts as a cam to release the piston and thereby pressurize the container. This also is a safety feature, for the piston is not readily releasable until the cam-cover is put into place and rotated.

The refill may, and preferably does, have an aluminum foil label seal over the opening in the center of the refill cover member, for shipping. This seal can be removed just prior to inserting the refill assembly into the outer casing, or the refill assembly may be inserted in the outer casing and urged against the valve with the seal intact, thereby permitting the valve stem to puncture the seal and at the same time sealing the refill to the valve by means of a sealing ring. Either way, the product inside the refill remains hermetically sealed until put into use. This is very useful for things such as medicines or chemicals that can be contaminated by prolonged exposure to air or sunlight.

The device of the present invention includes an outer case and an end cap which is threadably received by the outer case. A valve stem is provided in an upper end of the outer case. A refill assembly including a rigid cylindrical sleeve is receivable within the outer case and is securely positioned within the outer case by the bottom cap. The refill assembly includes an upper closure member which receives the valve stem of the outer case to permit the fluid contents of the refill assembly to be dispensed. A piston including at least one lock hook is slidably received within the rigid sleeve of the refill assembly. The piston is biased towards the upper closure of the rigid sleeve by a coil spring. A wiper seal which is preferably of a resilient material is provided immediately above the piston to effectively seal the product chamber of the refill assembly. The wiper seal includes an annular portion and an integrally joined disc portion. The at least one latch hook is releasably engaged in a lower closure portion of the cylindrical sleeve. The end cap includes an upwardly extending cam portion which releases the latch hook from the lower closure portion when the end cap is threaded onto the outer case. The end cap urges the refill assembly towards the valve stem so as to provide a communication between the product chamber and the valve. Simultaneuously, the end cap securely positions the refill assembly within the outer case and releases the biased piston to pressurize the product chamber.

BRIEF DESCRIPTION OF THE DRAWINGS

The invention will now be described with reference to the appended drawings wherein like reference numerals refer to like members and wherein:

FIG. 1 is a vertical sectional view of the device of the present invention immediately prior to threading the end cap onto the outer case;

FIG. 2 is a vertical sectional view of the device shown in FIG. 1 immediately after the end cap has been threaded onto the outer case;

FIG. 3 is an exploded view of the outer case and end cap of the device of the present invention;

FIG. 4 is a vertical sectional view of the disposable refill assembly of the device;

FIG. 5 is an end view through lines 5—5 of the bottom cap of FIG. 3;

FIG. 6 is a vertical sectional view of another disposable refill assembly of the device;

FIG. 7 is an exploded pictorial view of the refill assembly of FIG. 4; and

FIG. 8 is an end view through lines 8—8 of the outer case of FIG. 3.

DETAILED DESCRIPTION OF THE PRESENT INVENTION

With reference to FIG. 1 of the drawings, the device of the present invention includes an outer cylindrical casing 20 preferably of either metal or plastic and having an open bottom portion. An upper portion of the cylindrical casing 20 is closed and includes a neck portion 22. A standard aerosol valve assembly 24 is secured in an opening 26 of the upper portion of the cylindrical casing. The standard aerosol valve effectively closes the neck portion 22 of the cylindrical casing. The aerosol valve assembly includes a stem portion 28 which extends sufficiently so as to cooperate with an aperture in a refill assembly 30.

The refill assembly 30 includes a rigid cylindrical sleeve 32 having an upper sleeve portion 34 and a lower sleeve portion 36. The upper sleeve portion 34 includes a centrally disposed opening 38 having a deformable annular sealing member 40 which receives the valve stem 28. The valve stem 28 of the valve 24 is so designed as to have a gas tight fit in the opening 38 by means of the deformable sealing member 40 through which the valve stem must be pressed when the valve stem is assembled with the refill assembly.

The refill assembly 30 includes a biased piston 42 (see also FIG. 7). The piston 42 includes a pair of depending latch hooks 44. The latch hooks extend axially of the piston 42 and have tab portions 46 which extend radially inwardly of the depending latch hooks. A coil spring 48 is provided between the piston 42 and the lower sleeve portion 36. The spring 48 provides an upward biasing of the piston 42 and is sufficient to provide a pressurization of the product chamber for expelling the fluid contents through the valve 24. The particular characteristics of the spring bias are readily determined depending upon the desired pressurization of the product chamber. The pressurization of the product chamber depends upon such factors as the nature of the fluid product and the desired flow rate of the product through the valve.

The piston 42 includes a disc-like portion 50 having a diameter which is less than an inner diameter of the rigid cylindrical sleeve 32. An annular portion 54 is integrally attached to the disc-like portion of the piston by a shoulder portion 56. The annular portion 54 has a diameter which is substantially identical to the interior diameter of the rigid cylindrical sleeve. The annular portion 54 preferably has a thickness which permits the annular portion to extend between the spring 48 and the cylindrical sleeve 32. In this way, the annular portion of the piston helps to position the spring properly beneath the piston. The shoulder 56 of the piston receives a lower most portion of a wiper seal 58. The disc-like portion 50 of the piston is received within an interior cup shaped portion of the wiper seal 58. In this way, the piston adds structural stiffness to the wiper seal if the wiper seal is of a flexible, resilient material.

The wiper seal 58 includes an annular portion 60 which extends between the disc like portion 50 of the piston and the inner surface of the cylindrical sleeve 32. A disc-like portion 62 of the wiper seal is integrally formed with the annular portion of the wiper seal. A lower most end of the annular portion of the wiper seal includes a flange member which extends radially outwardly from the annular portion. In normal operation, the outwardly extending flange portion contacts the interior surface of the cylindrical sleeve 32 to effectively seal the product chamber.

The wiper seal is preferably of a resilient material and typically is of rubber or neoprene. The wiper seal bears against the walls of the sleeve 32 to make a gas-tight seal. The wiper seal is free to move upwardly under the influence of the piston 42.

The lower closure member 36 of the cylindrical sleeve 32 includes a centrally located raised portion 64. The raised portion 64 includes an opening corresponding to each latch hook of the piston 42. The corresponding openings of the lower closure member have a sufficient size to permit the tab portions of the latch hooks to be received through the openings. The latch hooks are preferably of a resilient material and are preferably urged towards one another. In this way, the piston 42 is releasably engaged with the lower closure member by means of the latch hooks 44. The bias provided by the coil spring 48 helps to retain the latch hooks 44 in engagement with the lower closure member. When the latch hooks are released from engagement with the lower closure member, the piston is urged upwardly to thereby pressurize the product chamber of the refill assembly.

An end cap 68 is releasably threaded onto the outer casing 20. The end cap 68 includes a centrally located raised portion 70 which acts as a cam to urge the depending locking hooks 44 away from one another. In this way, as the end cap 68 is threaded onto the outer case 20, the raised portion 70 urges the latching hooks away from one another and out of engagement with the lower closure portion of the cylindrical sleeve 32. Preferably, the piston is not released from engagement with the lower closure member until the end cap 68 is substantially fully threaded onto the outer case 20.

Threading the end cap 68 onto the outer case 20 simultaneously urges the assembly 30 upwardly within the outer case 20 to engage the valve assembly 24 with the annular sealing member 40. The end cap 68 also results in the secure positioning of the refill assembly within the outer casing. With reference to FIG. 3, intermittent threads are provided on a lower portion of the outer casing which correspond with intermittent threads of the bottom cap. The threads are preferably arranged so that the bottom cap is securely retained on the outer casing but is realeasable from the outer casing by unthreading the bottom cap.

With reference to FIG. 2, the disengagement of the piston with the lower closure portion is illustrated. An axial translation of the end cap 68 as a result of threading the end cap onto the outer case results in a radial separation of the depending locking hooks 44. Separation of the locking hooks permits the hooks to pass trough the openings in the lower closure member to thereby release the piston. When the piston is released, the coil spring 48 urges the piston and wiper seal upwardly within the sleeve of the refill assembly. In this way, the product chamber of the refill assembly is pressurized.

With reference to FIG. 3, the outer case 20 of the device is illustrated without the refill assembly positioned within the outer case. The intermittent threads 72 of the outer case are illustrated partially in dotted lines. The bottom cap 68 includes a corresponding plurality of the intermittent threads 74 which engage the intermittent threads of the outer case.

The refill assembly 30 with reference to FIG. 4 includes the outer sleeve 32 with upper and lower closure members 34, 36. The piston 42 and wiper seal 58 are releasably engaged with the lower closure member by means of the depending latch hooks. The coil spring 48 which is located between the piston and the lower closure member provides an upward bias for the piston.

The refill assembly of FIG. 4 is preferably obtained by first securing the lower closure member to the rigid cylindrical sleeve. The coil spring 48 may then be positioned above the lower closure member with the spring resting on a shoulder 76 of the lower closure member. The piston 42 may then be inserted axially through an upper end of the cylindrical sleeve 32. The piston 42 is urged downwardly to thereby compress the coil spring 48 until the depending locking hooks pass through the openings in the lower closure member and engage the lower closure member to releasably position the piston. The ends of the hooks 44 are pointed to facilitate insertion of the hooks through the opening of the lower closure member. The wiper seal 58 may then be inserted axially of the cylindrical sleeve 32 until the wiper seal is positioned atop the piston 42. At this time, the upper closure member of the cylindrical sleeve may be secured to the sleeve. The product chamber immediately above the wiper seal may be filled with the product fluid to a desired level. The deformable annular sealing member is then inserted in an opening of the upper sealing member to effectively seal the product chamber. A label seal may be provided on an outer end of the annular deformable seal. The label seal may be entirely removed immediately prior to inserting the refill assembly into the outer case, or the label seal 78 may be pierced by the stem of the valve assembly during assembly of the refill with the outer case.

With reference to FIG. 6, another refill assembly 130 includes a rigid cylindrical sleeve 32 provided with an upper closure member 134. The upper closure member 134 fits entirely within the end of the sleeve 32. The sleeve 32 may be crimped mechanically to securely engage the upper closure member 134 with the sleeve 32. A deformable annular seal 140 is provided in an opening 138 of the upper closure member 134. A piston 142 is provided within the sleeve 32 and is upwardly biased by a coil spring 148. The piston 142 includes a pair of depending latch hooks 144 having radially inwardly extending tab portions 146. The piston 142 includes an annular portion 154 and a disc like portion 150 which is integrally formed with the annular portion 154. The coil spring 148 engages the piston 142 in a shoulder recess formed by the annular portion 154 with the sleeve 32. The disc like portion 150 of the piston 142 extends upwardly from the annular portion 154 to provide a shoulder 156 to receive a wiper seal 158.

The wiper seal 158 is of a resilient material, preferably rubber or neoprene and includes a disc-like portion 162 and an annular portion 160. The wiper seal 158 engages the piston only at a bottom surface of the annular portion 160. The annular portion 160 and the disc-like portion 162 are formed integrally together in a single unit. The annular portion 160 together with the disc-like portion 162 provide a smooth cylindrical outer surface 163. The smooth outer cylindrical surface 163 contacts an inner surface of the sleeve 32 to provide a gas-tight seal for the product chamber.

A lower closure member 136 includes a centrally located raised portion 164. The raised portion 164 includes a plurality of openings corresponding to the latching hooks 144. The latching hooks pass through the openings of the raised portion 164 in a manner substantially similar to that of the refill assembly of FIG. 4. The radially inwardly extending tab portions of the latching hooks engage the lower closure member to releasably engage the piston with the lower closure member. The lower closure member 136 fits within the sleeve 32 and is secured to the sleeve by for example crimping the sleeve and lower closure member together. The lower closure member includes a shoulder 137 which receives a lowermost portion of the coil spring.

With reference to FIG. 7, the refill assembly is illustrated in an exploded view. The cylindrical sleeve portion 32 receives at its upper end the upper closure member 34. With reference also the FIG. 4, the upper closure member includes a lip portion 80 which permits the upper closure to be securely joined to the upper end of the cylindrical sleeve. The deformable seal 40 includes an annular recess 82 which facilitates insertion of the deformable seal in the opening of the upper closure member. The wiper seal 58 is positioned immediately above the piston 42 which has a pair of depending latch hooks 44. A coil spring 48 is located between the piston 42 and the lower closure member 36. The lower closure member, like the upper closure member includes a lip portion 84 to permit the lower closure member to be secured to the cylindrical sleeve 32.

With reference to FIG. 8, the outer case 20 includes a plurality of shoulders 86 (see also FIG. 3). The shoulders with reference also the FIGS. 1 and 2 maintain the refill assembly a desired distance away from an uppermost portion of the outer casing. The shoulder portions 86 add structural stability to the outer case.

With reference to FIG. 5, the intermittent threads 74 of the bottom cap are positioned circumferentially about the interior of the bottom cap. The raised portion 70 of the bottom cap is centrally located and is uniform throughout a circumference of the bottom cap.

In operation, the device is assembled by inserting a fresh refill assembly into the outer case 20 through a lowermost opening of the outer case. The refill assembly is inserted axially of the outer case until the deformable sealing member 40 comes into contact with the stem of the valve 24. The bottom cap 68 is then positioned onto the outer case 20 and is rotated so as to engage the intermittent threads of the bottom cap with the corresponding intermittent threads of the outer case. In this way, the refill assembly is urged axially to urge the valve stem through the deformable sealing member 40 to thereby provide a communication between the valve and the product chamber. Simultaneously, the bottom cap begins to urge the depending locking hooks radially away from one another to eventually release the biased piston 42. The bottom cap is rotated until the bottom cap is securely positioned on the outer case and the piston 42 has been released to pressurize the product chamber. In this way, the fluid contents of the product chamber may be dispensed through the valve 24 without requiring the use of a propellant gas.

To remove the refill assembly, the bottom cap is rotated in a reverse direction until the bottom cap is released from the outer case. The refill assembly may be readily removed from the outer case 20 at this time. The refill assembly may be discarded and a fresh refill assembly inserted in the manner described above. Alternatively, the refill assembly may be refilled either by the consumer or by the manufacturer through the deformable sealing member 40. Prior to filling the product chamber of an empty refill assembly, the piston 42 should be releasably engaged by the lower closure member. In most instances, however, the refill assembly will be discarded after the product chamber has been emptied.

The presently disclosed embodiment of the invention is intended to be considered in all respects as illustrative and not as restrictive, the scope of the invention being indicated by the appended claims rather than by the foregoing description and all changes which come within the meaning and range of equivalency of the claims are therefore intended to be embraced therein.

What is claimed is:

1. A reusable, fluid material dispensing device, comprising:
   an outer case;
   a refill assembly receivable within the outer case, including,
     a rigid cylindrical sleeve having an upper sleeve closure and a lower sleeve closure,
     a piston slidably received within the cylindrical sleeve and having at least one depending lock hook releasably received by the lower sleeve closure,
     wiper seal means for sealing an upper chamber of the refill assembly above the wiper seal means, the wiper seal means being slidably received within the cylindrical sleeve and located immediately adjacent to a top portion of the piston, and
     biasing means for urging the piston axially of the rigid cylindrical sleeve towards the upper sleeve closure;
   a bottom cap releasably engaged by the outer case and including release means for releasing the at least one lock hook of the piston from the lower sleeve closure when the bottom cap is engaged by the outer case.

2. The device of claim 1 further comprising: deformable sealing means for releasably sealing the upper chamber of the refill assembly, the deformable sealing means being provided in the upper sleeve closure; and
valve means for selectively supplying fluid from the upper chamber of the rigid cylindrical sleeve, the valve means being located in an upper portion of the outer case and communicating with the upper chamber of the refill assembly when the refill assembly is received within the outer case.

3. The device of claim 1 wherein
the biasing means includes a coil spring.

4. The device of claim 1 wherein
the wiper seal means includes a wiper seal made of a resilient material.

5. The device of claim 4 wherein the wiper seal is made of rubber or neoprene.

6. The device of claim 4 wherein
the wiper seal has an annular portion with a smooth, cylindrically shaped outer surface and a disc-shaped portion which is integrally connected to the annular portion.

7. The device of claim 4 wherein
the wiper seal has an annular portion with an outer surface having a generally decreasing diameter in the direction of an upper surface of the wiper seal and a disc-shaped portion which is integrally connected to the annular portion.

8. The device of claim 1 wherein
the bottom cap and outer case include corresponding intermittent threads to permit the releasable engagement of the bottom cap and outer case.

9. The device of claim 8 wherein
the piston includes two depending lock hooks which are located opposite one another and wherein
the bottom cap includes an upwardly extending cam to release the lock hooks from the lower sleeve closure.

10. A method of assembling a reusable fluid material dispensing device, comprising the steps of:
slidably inserting a refill assembly into an outer case until an upper sleeve closure of the refill assembly contacts a valve of the outer case;
threading a bottom cap onto a bottom portion of the outer case to thereby simultaneously engage the bottom cap on the outer case and urge the refill assembly towards an upper portion of the outer case whereby the valve of the outer case comes into fluid communication with an interior of the refill assembly; and
further threading the bottom cap onto the bottom portion of the outer case, to pressurize the interior of the refill assembly by releasing a piston of the refill assembly, the piston being released substantially immediately before the bottom cap is securely threaded onto the outer case.

11. A fluid material dispensing device, comprising:

a separate, disposable, one-use refill assembly, consisting essentially of a rigid cylindrical sleeve and within said sleeve a supply of fluid material to be dispensed, said refill assembly having an elastically sealable aperture in the top thereof and having a pressure-supplying assembly in the bottom thereof, the pressure-supplying assembly consisting essentially of a piston means for urging the supply of fluid within the sleeve, a bottom member, a compression spring mounted between said bottom member and said piston means and locking means for releasably restraining said compression spring in a compressed state, the locking means being carried by the piston means; and a re-usable dispenser assembly consisting essentially of:

a casing having an open bottom and a top wall provided with an opening, said casing being dimensioned to contain said refill assembly;

an aerosol valve assembly secured in said opening;

a bottom cap for said casing, said bottom cap being capable of movement relative to said casing and carrying unlocking means for unlocking said locking means in response to said movement and said aerosol valve assembly including a stem portion adapted to be inserted into the interior of said refill assembly through the elastically sealable aperture.

12. The device defined in claim 11, wherein said locking means comprises hook members depending from said piston means, said hook members terminating in inturned hooks, said bottom member having a bottom wall provided with slots dimensioned to receive said hook members and to releasably retain said hooks.

13. The device defined in claim 12, wherein said unlocking means comprises an indentation of the bottom cap having the form of a cam and adapted to be inserted between said hook members.

14. The device defined in claim 11, wherein said movement comprises rotary movement.

15. The device defined in claim 14, wherein said cap is threadably connectible to said casing, said movement defined by threading of said cap onto said casing.

16. The device as defined in claim 11, wherein said cap is securable to said casing by means of said movement.

* * * * *